United States Patent [19]
Koch

[11] Patent Number: 5,510,064
[45] Date of Patent: Apr. 23, 1996

[54] METHOD OF FORMING A CUSTOM MOLDED CERVICAL CAP

[76] Inventor: James P. Koch, 211 Sargent Rd., Brookline, Mass. 02146

[21] Appl. No.: 989,089

[22] Filed: Dec. 11, 1992

[51] Int. Cl.⁶ .......................... B29C 33/42; B29C 45/76
[52] U.S. Cl. .......................... 264/40.1; 264/222; 264/259
[58] Field of Search ................... 425/2; 264/222, 264/268, 275, 334, 511, 250, 255, 40.1, 267, 259

[56] References Cited

U.S. PATENT DOCUMENTS

| | | | |
|---|---|---|---|
| 3,952,737 | 4/1976 | Lipfert et al. | 128/127 |
| 4,311,543 | 1/1982 | Strickman et al. | 156/224 |
| 4,363,318 | 12/1982 | Goepp et al. | 128/130 |
| 4,401,534 | 8/1983 | Goepp et al. . | |
| 5,027,830 | 7/1991 | Koch | 128/841 |
| 5,123,424 | 6/1992 | Koch | 128/841 |

FOREIGN PATENT DOCUMENTS

PCT/US93/12108  3/1994  WIPO .

Primary Examiner—Jan H. Silbaugh
Assistant Examiner—Angela Ortiz
Attorney, Agent, or Firm—Fish & Richardson

[57] ABSTRACT

A method is provided of forming a cervical cap in situ, i.e., within a patient's body, which cap will substantially completely conform to the shape of the patient's cervix, allowing the cap to be left in place over an extended period of time. The method includes the steps of positioning a snugly fitting rim member around the patient's exocervix, mounting a shell member, having an aperture, onto the rim member such that the rim member, shell member and exocervix define a cavity, and injecting a curable material through the aperture to substantially fill the cavity. After the curable material is allowed to harden, the entire assembly is removed from the patient and the shell removed from the cured material.

7 Claims, 6 Drawing Sheets

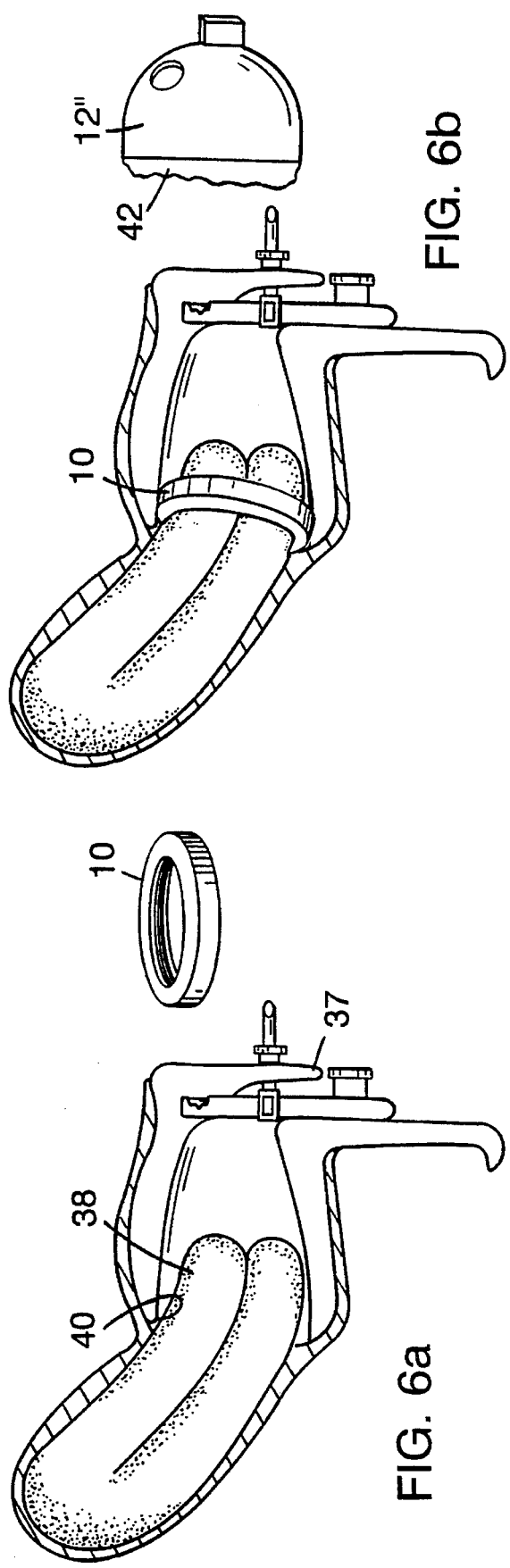
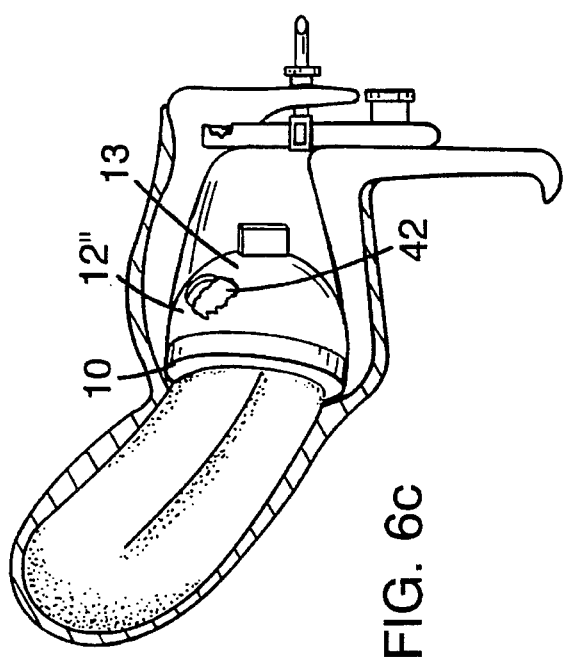
FIG. 6a
FIG. 6b
FIG. 6c

METHOD OF FORMING A CUSTOM MOLDED CERVICAL CAP

BACKGROUND OF THE INVENTION

The invention relates to methods of forming cervical caps.

Cervical caps, i.e., cap-shaped devices which fit over a patient's cervix to prevent ingress of sperm into the patient's uterus, have long been used for contraception. Most of these devices are not custom molded to the shape of the individual patient's cervix, but are merely provided in several sizes. While many of these non-customized devices provide good contraception, they cannot be left in for extended periods of time, and typically must be removed after as little as 48 hours, making them hardly more convenient than diaphragm-type contraceptive devices.

Other cervical caps have been custom molded by a three-step process, typically requiring two visits to the clinician before the cap can be completed. This process involves the forming of a casting of the patient's cervix, typically using an alginate or polysiloxane impression material, making a plaster or stone model of the cervix using the casting, and thermoforming of a thermoplastic, e.g., a styrene-butadiene block copolymer, over the model. Custom forming of the cap allows the cap to conform very closely to the cervix, preventing buildup of fluids and reducing the possibility of infection, thus allowing the patient to keep the cap in place for much longer periods of time. For the cap to be left in place however, it is necessary to provide a one-way valve in the cap to allow egress of fluids from the uterus, while preventing any ingress of sperm. The design of some of these valves has reduced the contraceptive effectiveness of the cap.

Another method of forming a cervical cap in situ is disclosed in U.S. Pat. No. 4,007,249. According to this method, a layer of curable elastomeric material is applied directly to the surface of the patient's cervix and allowed to cure in place.

U.S. Pat. No. 5,123,424 proposes yet another method for forming a cervical cap in situ. In this method, a cervical cap, which includes a rim and a dome, is fitted to the patient's cervix, such that a gap is formed between the dome and cervix, and a biocompatible material is injected into the gap while the cap is in place. The finished cervical cap includes the cervical cap which was fitted to the patient and the biocompatible material, which bonds to the inner surface of the dome.

SUMMARY OF THE INVENTION

The invention features, in one aspect, a method of forming a cervical cap in situ, i.e., within a patient's body. The custom molded cap thus formed will substantially completely conform to the shape of the patient's cervix, allowing the cap to be left in place over an extended period of time. The method is easily performed, and typically requires only a single visit to the clinician.

The method of the invention includes the steps of positioning a snugly fitting rim member around a patient's exocervix, mounting a shell member, having an aperture, onto the rim member such that the rim member, shell member and exocervix define a cavity, and injecting a curable material through the aperture to substantially fill the cavity. After the curable material is allowed to harden, the entire assembly (rim, shell and curable material) is removed from the patient and the shell is removed from the cured material. The finished cap (formed from the rim and cured material) may then be used by the patient.

In preferred embodiments, the rim member is formed of a resilient biocompatible elastomeric material, preferably silicone rubber, and includes one or more ridges on its inner surface so that the rim positively grips the exocervix. It is further preferred that the shell member be translucent, to enable the clinician to observe when the cavity is substantially filled, and that the shell include a grip portion extending from its outer surface to allow the shell to be easily maneuvered into place and the assembly removed from the patient.

In another embodiment, the method includes the steps of positioning a snugly fitting rim member around the patient's exocervix, injecting a curable material over the exocervix such that it bonds to the entire circumference of the rim and covers the entire surface of the exocervix that is within the circumference of the rim. After the curable material has hardened, the cap, formed by the rim and curable material, may be removed from the patient's body. The cap will have an irregular outer surface. If a smooth surface is desired, the outer surface may be built up with additional curable material, e.g., by placing a shell member, partially filled with curable material and having an aperture so that excess material can escape, over the outer surface of the cap.

In another aspect, the method of the invention includes the steps of positioning a snugly fitting rim member around the patient's exocervix, providing a shell member having an aperture and containing an excess of a curable material, and mounting the shell member on the rim member. The excess curable material extrudes out of the aperture, the curable material is allowed to harden, and the shell member, rim and curable material are removed from the patient. The shell member may then be removed from the curable material, and the finished cap formed from the rim and curable material used by the patient.

In another aspect, the invention features a cervical cap formed by any of the above methods. In preferred embodiments, the cap includes a flow control means, e.g., a one-way valve, to allow egress of fluids from the uterus when the cap is in use in the patient's body. In one embodiment, the means comprises an aperture in the cap and a flutter valve, fused to the cap around the aperture.

In another aspect, the invention features a kit for use by a clinician in forming a custom cervical cap in situ in a patient's body. In one embodiment, the kit includes a rim member, a curable material, and a means for applying the curable material. In another embodiment, the kit further includes a shell member dimensioned to be mounted on the rim member. In preferred embodiments, the kit includes a plurality of rim members, having different inner diameters, such that a plurality of rim members can be tried on the patient until one is found which snugly fits the patient's exocervix, and a plurality of shell members, each shell member dimensioned to fit a corresponding rim member. Preferably, the inner diameters of the rim members are from about 22 to 32 mm; more preferably, about 10 rim members are provided, with inner diameters 1 mm apart, the smallest of the rim members having an inner diameter of about 22 mm. In a further preferred embodiment, the means for applying the cured material comprises a syringe, preferably dimensioned to extend out of the patient's body when in use. In the embodiment in which the kit includes a shell member, the shell member has the preferred features described with reference to the method, and the syringe preferably has an angled tip to facilitate insertion into the aperture in the shell member. The kit may also include a forceps, a large aperture vaginal speculum, a lateral vaginal speculum, and instructions for use of the kit.

Other features and advantages of the invention will be apparent from the Description of the Preferred Embodiments thereof, and from the claims.

BRIEF DESCRIPTION OF THE DRAWINGS

FIG. 1a shows a cross sectional view of the rim member shown in FIG. 1, taken along line 1a—1a.

FIG. 3a shows a cross-sectional view of the cap shown in FIG. 3, taken along line 3a—3a.

FIGS. 6a–6c show a method for forming a custom cervical cap according to another alternate embodiment of the invention.

DESCRIPTION OF THE PREFERRED EMBODIMENT

Figure 1:
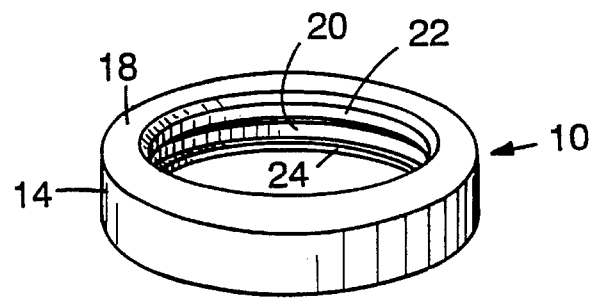
FIG. 1 shows a perspective view of a rim member according to one embodiment of the invention.
Figure 1A:
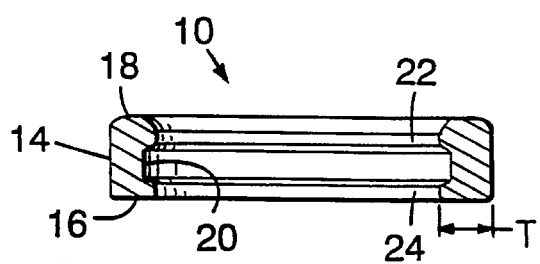
Figure 2:
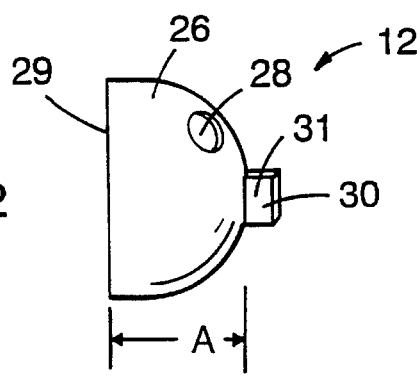
FIG. 2 shows a shell member according to one embodiment of the invention.

Preferred rim and shell members 10 and 12 are shown in FIGS. 1, 1a and FIG. 2, respectively. The preferred rim member 10 has a smooth, substantially vertical outer wall 14, a smooth, substantially horizontal lower wall 16, a convex upper surface 18, and a concave inner wall 20, defined by upper and lower ridges 22, 24. Ridges 22 and 24 extend around the entire circumference of the rim, to hold the rim firmly in place against the exocervix both during molding of the cap and during use of the finished cap. The rim member has an inner diameter which is sized to fit snugly over the exocervix of the patient who will use the finished cap, typically from about 20 to 35 mm, and an outer diameter of about 26 to 47 mm. The thickness of the rim (dimension T in FIG. 1A) preferably remains constant as the inner diameter is varied to fit the individual patient, i.e., rims having larger inner diameters have correspondingly larger outer diameters. The rim member is preferably made of a flexible, resilient biocompatible material, e.g., silicone. Suitable silicone elastomers are available from Dow Corning and Factor II.

A preferred shell member 12 includes hemispherical shell 26, aperture 28 disposed approximately halfway between the edge 29 and apex 31 of the hemisphere, and a gripping tab 30 disposed approximately at apex 31. Shell 26 is preferably formed of a material which is translucent or transparent, and which the curable material to be used will not adhere to, e.g., ethylene vinyl acetate or cellulose acetate. Preferably, the shell has a wall thickness of from about 1 to 3 mm, and has an inner diameter equal to (for a pressure fit) or slightly larger, e.g., about 1 to 3 mm larger, than the outer diameter of the rim member. Thus, for the preferred rim member dimensions, the shell will have an outer diameter of from 27 to 50 mm. The depth of the shell (dimension A in FIG. 2) is preferably determined for each patient. The preferred depth of the shell is from 2 to 10 mm greater than the protrusion of the patient's cervix from the rim when the rim is in place, or typically from about 10 to 25 mm total depth. Gripping tab 30 is preferably an approximately rectangular member, extending, in a plane approximately perpendicular to the plane of the edge of the hemisphere, from approximately the apex of the hemisphere. Aperture 28 preferably has a diameter of from about 4 to 8 mm.

Figure 3:
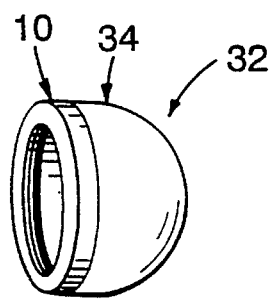
FIG. 3 shows a perspective view of a cap according to one embodiment of the invention.
Figure 3A:
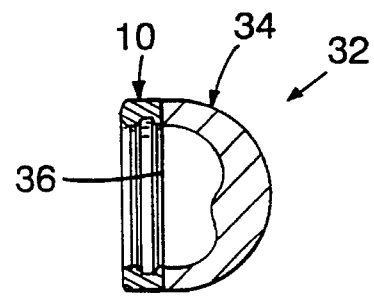

Following the method illustrated in FIGS. 4a–4d, or a similar method, a cap 32 is obtained as shown in FIGS. 3 and 3a. Cap 32 comprises rim 10, and dome 34 of biocompatible material bonded to surface 16 of rim 10. Materials suitable for use in forming dome 34 are those which will cure at the patient's body temperature, are biocompatible, and will adhere to the rim. Suitable materials include but are not limited to silicones and siloxanes. A suitable silicone is SILASTIC 382 silicone, available from Dow Corning. As shown in FIG. 3a, inner surface 36 of dome 34 is contoured to conform virtually identically to the surface of the patient's exocervix.

A method of forming a cervical cap in situ, according to a preferred embodiment, is shown in FIGS. 4a–4d.

Figure 4A:
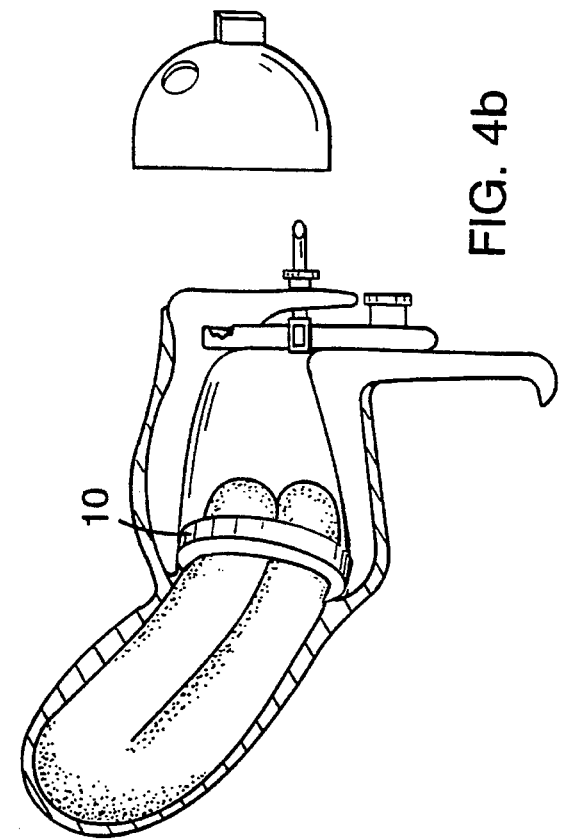
FIGS. 4a–4d show a method for forming a custom cervical cap according to one embodiment of the invention.

As shown in FIG. 4a, the patient's exocervix 38 is first exposed, typically by using a speculum 37 in a standard manner. A single speculum may not adequately expose the exocervix, in which case two speculums may be used, a standard vaginal speculum and a lateral vaginal speculum. The standard vaginal speculum will preferably have a large aperture, and the lateral speculum may need to be modified for use in the methods of the invention. To fully expose the exocervix may require a lateral speculum which is slightly wider and considerably longer than those which are commercially available, and which has straight rather than curved tips. If the clinician finds that the patient's cervix is not oriented so that it is facing approximately towards the clinician, the cervix can be so positioned by gently repositioning the uterus. A rim 10 of suitable size, i.e., one which fits exocervix 38 snugly, is selected, by trying different sizes, if necessary, and placed over the exocervix such that rim surface 18 is adjacent or near the fornices vaginae 40. The rim and/or cervix may be gently manipulated until this is achieved, and the protrusion of the exocervix from the rim is maximized. Forceps are generally used to position the rim. The tips of the forceps may be enlarged, e.g., with plastic blocks, to allow the rim to be more easily pressed onto the exocervix. The protrusion of the exocervix may then be measured, to determine the depth of the shell, as discussed above.

Figure 1B:
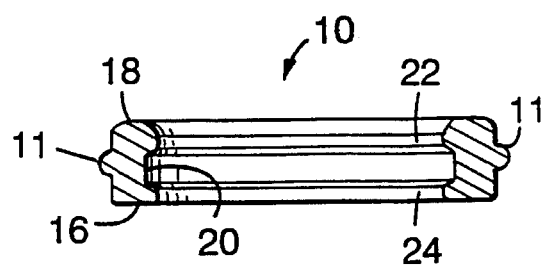
FIG. 1b shows a cross sectional view of a rim member according to an alternate embodiment of the invention.
Figure 4B:
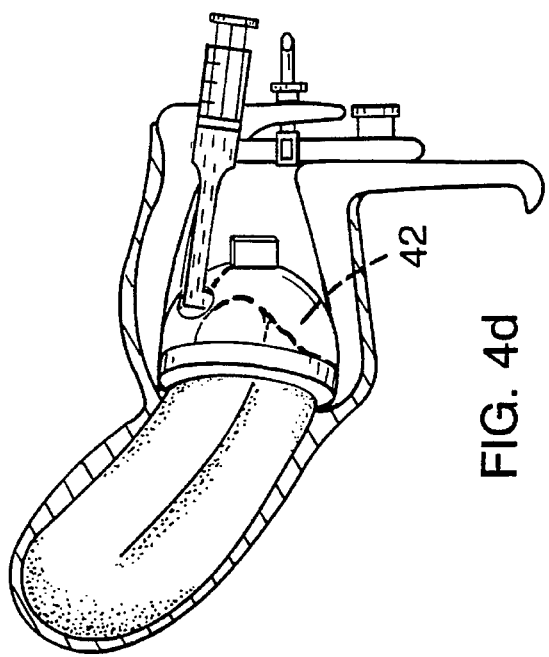
Figure 4C:
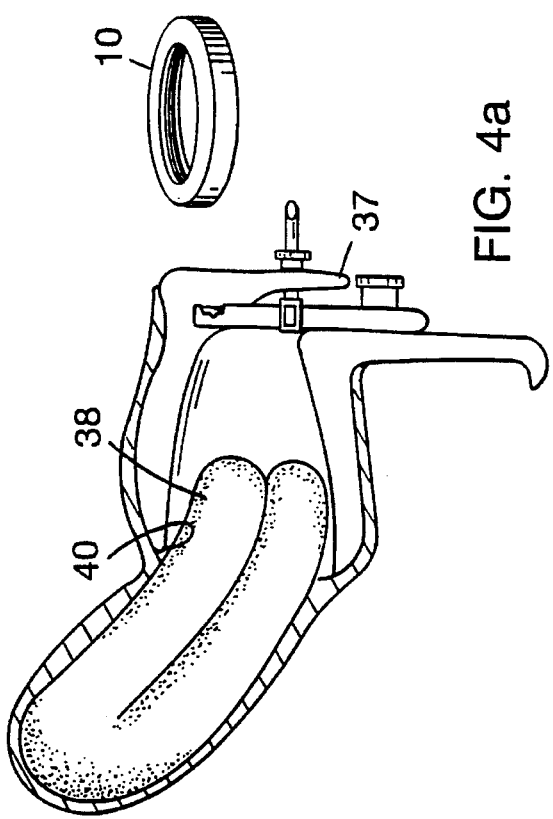

As shown in FIGS. 4b and 4c, a shell 12 having an inner diameter appropriate to fit the outer diameter of the selected rim is then fitted onto the rim, preferably snapfit, such that shell 12, rim 10, and the patient's exocervix 38 define cavity 13. Because it is desirable that the shell only slide partially over the rim, and that the shell overlap the rim by a constant amount around the circumference of the rim, a flange 11 may be provided on the outer surface of the rim (see FIG. 1b) to act as a stop to prevent further movement of the shell. Curable material 42 is provided in a suitable dispensing device, e.g., a syringe 44 as shown. Syringe 44 preferably includes an angled tip 46, to allow the syringe to be easily inserted into aperture 28 in the shell without excessive movement of the syringe within the patient. A length of bent, semiflexible tubing may be attached to a standard syringe to form angled tip 46.

Figure 4D:
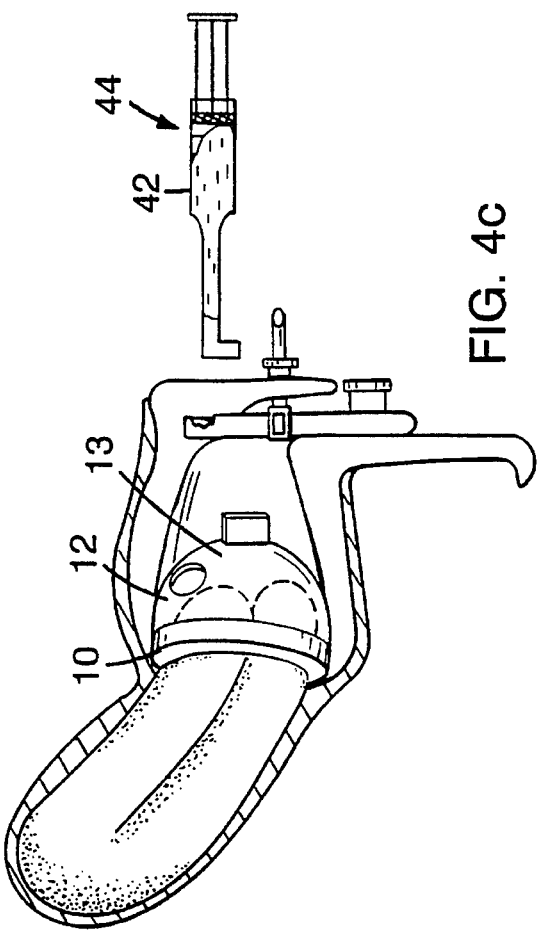

As shown in FIG. 4d, the curable material 42 is dispensed from the syringe 44, through the aperture 28 and into cavity 13, until cavity 13 is substantially or entirely filled. The degree to which the cavity is filled can be determined by observing the translucent shell. If an opaque shell is provided, the required volume of curable material can be easily calculated based on the volume of the shell.

After the curable material has been allowed to harden, typically from about 5 to 15 minutes, depending upon the setting time of the material used, the entire assembly (rim, shell, and cured material) is removed together (not shown) and the shell is removed from the cured material. The cap is then ready for use by the patient.

Figure 5B:
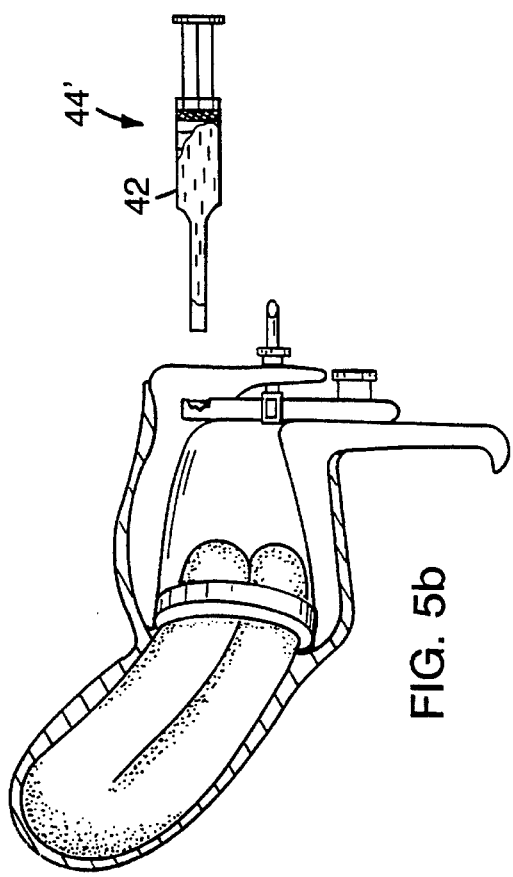
FIGS. 5a–5f show a method for forming a custom cervical cap according to an alternate embodiment of the invention.
Figure 5D:
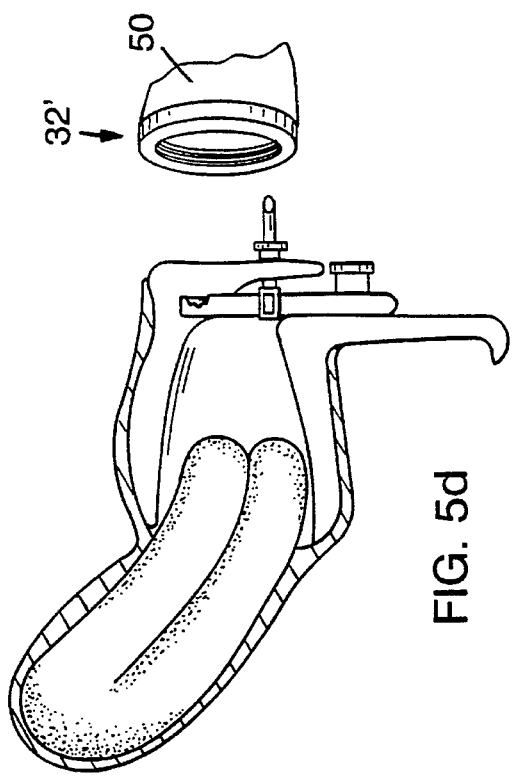
Figure 5A:
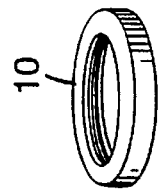
Figure 5A:
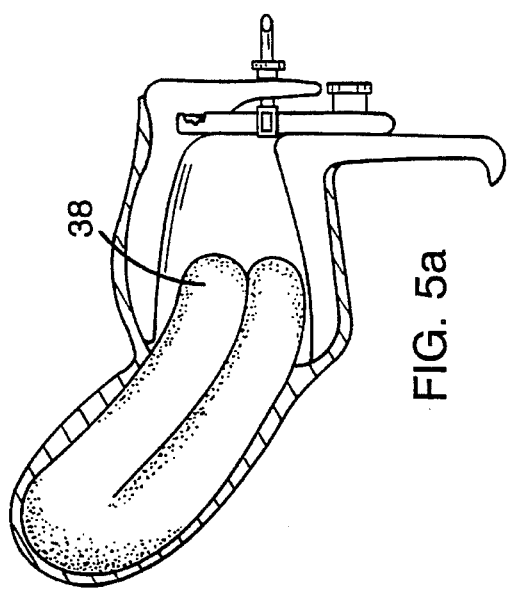
Figure 5C:
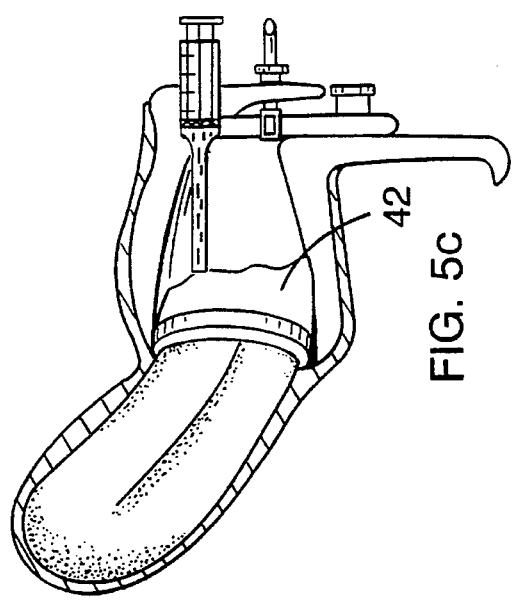
Figure 5E:
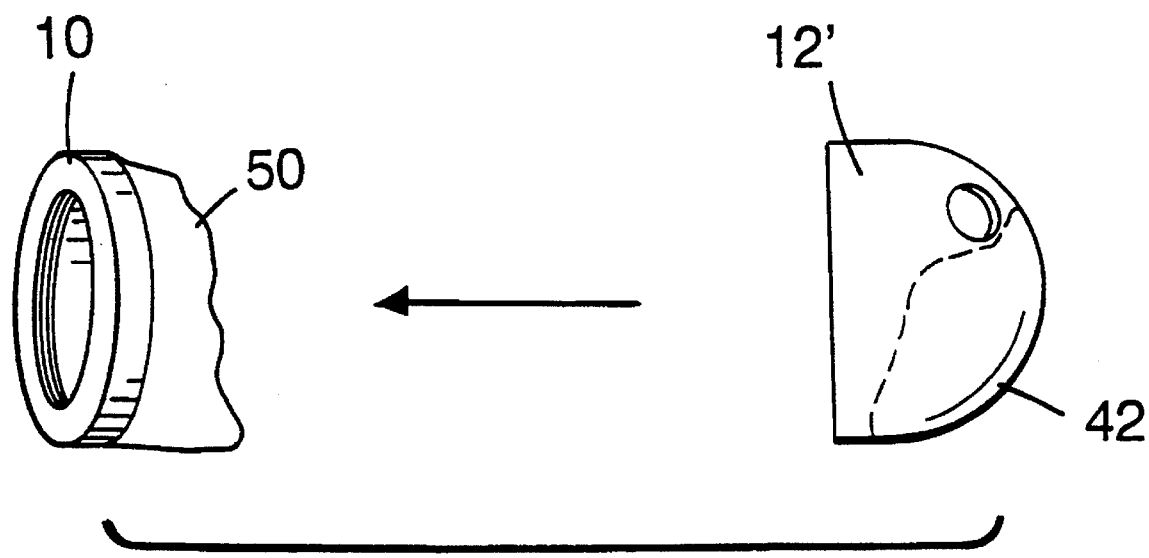
Figure 5F:
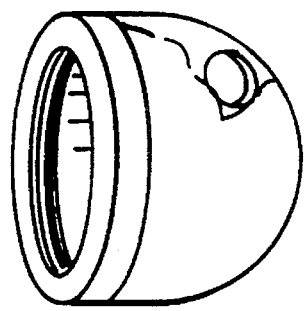

A method according to an alternate embodiment of the invention is shown in FIGS. 5a–5d. According to this method, a rim is again provided and the exocervix is exposed (FIG. 5a), and the rim is applied to the exocervix (FIG. 5b), as described above for the method shown in FIGS. 4a–4d. In this embodiment, however, curable material 42 in syringe 44' (FIG. 5b) is applied to the patient's exocervix, without a shell being applied to the rim (FIG. 5c). After the curable material has hardened, the cap 32', formed by the rim and the curable material bonded thereto, is removed from the patient (FIG. 5d). Cap 32' can then be used by the patient, if the irregular surface 50 is not objected to, provided that the entire area within the rim is covered with a continuous layer of hardened curable material. If desired, however, additional curable material can be applied to surface 50 of the cap, to make the surface smoother. This may be accomplished by partially filling shell member 12 with curable material 42, and placing the shell member over the cap (FIGS. 5e and 5f). After the curable material has hardened, the shell can be removed and the cap used.

Figure 7:
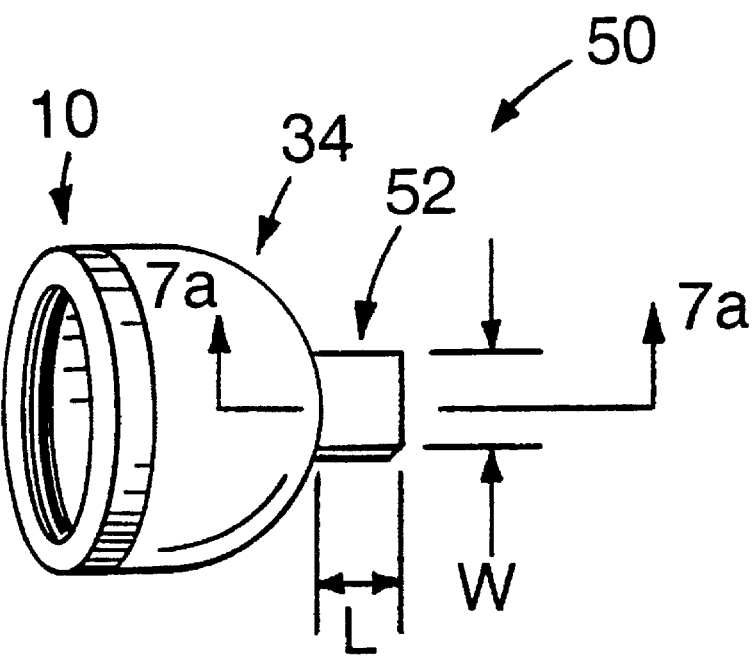
FIG. 7 is a front view, and FIG. 7a a side cross-sectional view, of a custom cervical cap including a valve according to one embodiment of the invention.
Figure 7A:
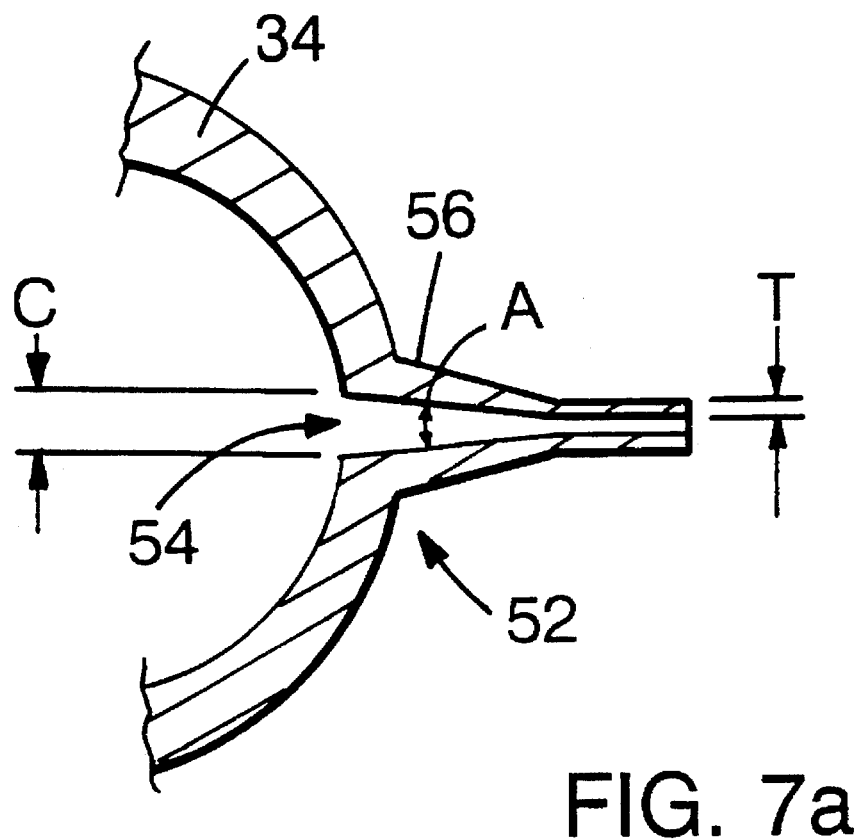

As shown in FIG. 7, the finished cap may include a valve 52. The valve is typically added to the cap after the cap is formed, although a valve could be included during molding, provided the custom fit of the cap is not interfered with. Valve 52, referred to herein as a "flutter valve", comprises a thin envelope of elastomeric material, open where it meets the cap and at its opposite end. Valve 52 extends from cap 50 near the apex of the cap, surrounding aperture 54 (see FIG. 7a). Prior to attachment of valve 52, aperture 54 is formed in cap 50. Valve 52 is then attached to cap 50 in an impermeable manner, preferably by fusing the two materials together, e.g., using a primer. Preferred dimensions of the valve shown in FIGS. 7 and 7a are approximately as follows: W=10 to 15 mm, L=20 to 30 mm, angle A=30 to 45 degrees. Aperture 54 in cap 52 preferably has a diameter C of about 2 to 10 mm. The wall thickness T of the valve is preferably about 0.5 to 1 mm. The opening at the end of the valve is preferably 1 mm or less. The valve may, however, have any dimensions which allow egress of fluid from the uterus while preventing ingress of sperm. The valve need not be a flutter valve, as shown, but could be, e.g., a long, thin tube of a material which would tend to remain collapsed, or other type of one-way valve. The valve will allow the cap to be worn for extended periods of time, by enabling menstrual and other bodily fluids to pass through the cap.

Other embodiments are within the claims.

I claim:

1. A method of forming a custom-fitted cervical cap in situ, within a patient's body, comprising the steps of
   (a) positioning a first rim member, having a predetermined inner diameter, around the patient's exocervix;
   (b) determining whether the rim member fits snugly around the patient's exocervix;
   (c) if the first rim member does not fit snugly, removing the first rim member and positioning a second rim member, having an inner diameter smaller than that of the first rim member, around the patient's exocervix;
   (d) repeating steps (b) and (c) for each successive rim member, until a rim member is found which fits the exocervix snugly, said rim member including one or more ridges on its inner surface to securely grip the exocervix;
   (e) selecting a shell member which is dimensioned to be mounted sealingly onto the rim member which fits the exocervix snugly, the shell member including an aperture;
   (f) mounting the shell member onto the rim member such that the rim member, the shell member and the exocervix define a cavity;
   (g) injecting a curable material through the aperture to substantially fill the cavity; and
   (h) allowing the curable material to harden and removing the shell member, the hardened curable material and the rim member, in combination, forming the custom-fitted cervical cap.

2. A method of claim 1 further comprising the steps of, after the curable material has hardened, removing the assembly defined by the rim member, the shell and the curable material from the patient, and removing the shell from the hardened curable material.

3. A method of claim 1, wherein the rim member is formed of a resilient biocompatible elastomeric material.

4. A method of claim 3 wherein the rim member is silicone rubber.

5. A method of claim 1 wherein the shell member is translucent.

6. A method of claim 1 wherein the curable material is a silicone or siloxane.

7. A method of claim 1 wherein the shell includes a grip portion extending from its outer surface.

* * * * *

UNITED STATES PATENT AND TRADEMARK OFFICE
CERTIFICATE OF CORRECTION

PATENT NO. : 5,510,064
DATED : April 23, 1996
INVENTOR(S) : James P. Koch

It is certified that error appears in the above-indentified patent and that said Letters Patent is hereby corrected as shown below:

Column 4, line 13, correct the spelling of "illustrated".

Signed and Sealed this

Twenty-fourth Day of September, 1996

Attest:

BRUCE LEHMAN

Attesting Officer

Commissioner of Patents and Trademarks